(12) United States Patent
Mclean et al.

(10) Patent No.: US 9,616,146 B2
(45) Date of Patent: Apr. 11, 2017

(54) DAIRY FARM FLUID LINE TREATMENT

(71) Applicant: 2178450 Ontario Inc., Shanty Bay (CA)

(72) Inventors: Brian Mclean, Thornton (CA); Peter Strain, Shanty Bay (CA)

(73) Assignee: 2178450 Ontario Inc., Shanty Bay (CA)

( * ) Notice: Subject to any disclaimer, the term of this patent is extended or adjusted under 35 U.S.C. 154(b) by 310 days.

(21) Appl. No.: 14/294,474

(22) Filed: Jun. 3, 2014

(65) Prior Publication Data

US 2014/0356227 A1 Dec. 4, 2014

Related U.S. Application Data

(60) Provisional application No. 61/830,347, filed on Jun. 3, 2013.

(51) Int. Cl.
*A61L 2/20* (2006.01)
*A01J 7/02* (2006.01)

(52) U.S. Cl.
CPC .............. *A61L 2/202* (2013.01); *A01J 7/02* (2013.01)

(58) Field of Classification Search
CPC .............. A61L 2/202; A01J 7/02; A01J 5/00
USPC .................... 422/3, 111; 119/14.01
See application file for complete search history.

(56) References Cited

U.S. PATENT DOCUMENTS

| | | | |
|---|---|---|---|
| 3,421,625 A | 1/1969 | Fritz | |
| 5,236,722 A | 8/1993 | Schroeder | |
| 5,302,356 A | 4/1994 | Shadman et al. | |
| 6,006,387 A | 12/1999 | Cooper et al. | |
| 6,132,629 A | 10/2000 | Boley | |
| 6,287,515 B1 | 9/2001 | Koosman et al. | |
| 6,723,293 B2 | 4/2004 | Jensen | |
| 6,726,817 B1 | 4/2004 | Gruett | |
| 7,488,424 B2 | 2/2009 | Gruett et al. | |
| 7,563,361 B2 | 7/2009 | Gruett et al. | |
| 8,163,173 B1 | 4/2012 | Dellecave et al. | |

(Continued)

FOREIGN PATENT DOCUMENTS

| | | |
|---|---|---|
| EP | 2433909 A1 | 3/2012 |
| EP | 2433909 A1 | 3/2012 |

(Continued)

OTHER PUBLICATIONS

Furrowpump web site http://www.furrowpump.com/Resources/toptenfactorstoconsiderozone.pdf, May 1998.

(Continued)

*Primary Examiner* — Sean E Conley
(74) *Attorney, Agent, or Firm* — Gilbert's LLP; Matthew D. Powell

(57) ABSTRACT

A fluid line treatment kit for a dairy farm milking system having a vacuum subsystem for imparting vacuum within a fluid line is provided. The fluid line treatment kit includes at least one ozone gas source; a conduit associated with each ozone gas source configured to convey ozone gas to within the fluid line at a respective location; and a control system configured to trigger each ozone gas source to produce ozone gas while the vacuum subsystem is actuated. Vacuum imparted by the vacuum subsystem in the fluid line draws ozone gas via the at least one conduit into and through the fluid line.

4 Claims, 4 Drawing Sheets

(56) References Cited

U.S. PATENT DOCUMENTS

| | | |
|---|---|---|
| 9,199,231 B2 | 12/2015 | Strain |
| 2002/0166817 A1 | 11/2002 | Gruett |
| 2004/0016706 A1 | 1/2004 | Minnix |
| 2004/0026451 A1 | 2/2004 | Jones |
| 2004/0055969 A1 | 3/2004 | Barnes |
| 2004/0154998 A1 | 8/2004 | Minnix |
| 2005/0236338 A1 | 10/2005 | Minnix |
| 2006/0027463 A1 | 2/2006 | Lavelle et al. |
| 2009/0145820 A1 | 6/2009 | Gruett et al. |
| 2010/0200522 A1 | 8/2010 | Tischendorf et al. |
| 2011/0203978 A1 | 8/2011 | Handy |
| 2012/0305488 A1 | 12/2012 | Gruett et al. |
| 2013/0075313 A1 | 3/2013 | Handy |
| 2013/0098845 A1 | 4/2013 | Gruett et al. |
| 2013/0104742 A1 | 5/2013 | Deo et al. |

FOREIGN PATENT DOCUMENTS

| | | | |
|---|---|---|---|
| GB | 191019621 | * | 0/1910 |
| WO | WO 01/54786 A2 | | 2/2001 |

OTHER PUBLICATIONS

Lenntech web page—ozone injection techniques http://www.lenntech.com/systems/ozone/injection/ozone-injection.htm, Nov. 7, 2014.

Quality Water Treatment web page, ozone water treatment system http://www.qualitywatertreatment.com/ozone_systems.htm, Nov. 7, 2014.

Well Water—Water Technology Magazine 2003 http://www.cwtozone.com/uploads/SalesDocs/Markets/Potable%20Water%20/Papers/New%20Articles/W.

Well Water—Water Technology Magazine 2003 http://www.cwtozone.com/uploads/SalesDocs/Markets/Potable%20Water%20/Papers/New%20Articles/Well%20Water%20WTM.

Office Action Issued Aug. 1, 2014 by Canadian Intellectual Property Office in connection wiht CA2836680.

* cited by examiner

DAIRY FARM FLUID LINE TREATMENT

CROSS REFERENCE TO RELATED APPLICATION

This application claims priority under 35 U.S.C. 119(e) from U.S. Provisional Patent Application Ser. No. 61/830,347 filed on Jun. 3, 2014.

FIELD OF THE INVENTION

The present invention relates generally to dairy farm milking systems, and more particularly to treating fluid such as air passing through a fluid line of a dairy farm milking system using ozone gas.

BACKGROUND OF THE INVENTION

A dairy farm milking system is for harvesting milk from animals such as cows and goats. Such a system is typically installed within a barn or other building, and is configured to extract, convey and temporarily store the milk being harvested from the animals.

Various dairy farm milking systems are known. For example, a milking parlour typically refers to a system in which each animal enters a milking station for extraction of their milk, whereas a milking stall system is one in which each animal is positioned in a respective stall and the producer (i.e., a farmer) goes from stall to stall to extract the milk Some dairy farm milking systems are primarily automated, using robotics, lasers and/or image-capture devices to align extraction equipment such as a milking unit to the particular animal being milked Other dairy farm milking systems are configured such that manual application of the milking unit to the animal is required.

A common dairy farm milking system includes at least one milking unit, a fluid line having an air section and a liquid section, a receiver jar, a vacuum subsystem, and a milk bulk tank.

Each milking unit is generally configured to couple with, and extract milk from, the udder of the animal. The milking unit is arranged to be in fluid communication with both the air section and the liquid section of the fluid line, and employs vacuum imparted to the fluid line by the vacuum subsystem to coax milk out of the teats of the animal for conveying into and through the liquid section of the fluid line. During the coaxing, continuous vacuum is applied via the air section of the fluid line to the teat cups of the milking unit that respectively receive the teats to ultimately create a pressure difference across each teat canal thereby to coax the milk from the teat. In order to relieve the animal's teat from constant pressure, atmospheric air is periodically admitted into the milking unit at a pulsation rate of about once per second.

The milk extracted from the animal is conveyed under vacuum through the liquid section of the fluid line to a receiver jar, and is in turn conveyed to the milk bulk tank for cooling and storage. The air section of the fluid line is also in fluid communication with the receiver jar. It is at the receiver jar that the air and liquid sections of the fluid line meet. However, due to the respective locations at which each of the air and liquid sections enter the receiver jar, liquid in the liquid section generally cannot enter into the air section.

While there are various cycles that could be employed for milking and cleaning fluid lines, it is generally the case that, prior to and after milking, chemical and water rinses with chlorine or other treatment materials are conducted to cleanse the fluid line of bacteria and any other unwanted elements so that they are not carried by the milk into the milk bulk tank.

In the case of an animal such as a cow or goat, the udder extends below the animal close to the hind legs and the floor on which the animal is standing. During milking, the milking unit must therefore be positioned accordingly. However, the floor on which the animal is standing is typically at least somewhat soiled with the animal's fecal matter and urine which can, along with the surrounding air, contain high levels of bacteria. Furthermore, during milking the animal is generally free to expel fecal matter and urine, and animals can jostle the milking unit with their legs. As such, the inventors have considered that the milking unit admitting atmospheric air into the teat cup at the pulsation rate can, in doing so, also admit significant amounts of air borne bacteria into the stream of milk being extracted.

Furthermore, the inventors have also considered that air borne bacteria may also be admitted into the stream of milk via the vacuum subsystem. In particular, the vacuum subsystem may include one or more vacuum pumps that are coupled to the fluid line for imparting the vacuum to the fluid line when actuated, and one or more vacuum regulators for permitting atmospheric air to enter into the fluid line to regulate vacuum pressure levels within the fluid line. In the event that a particular vacuum regulator is positioned near to areas having high levels of air borne bacteria within the building or even outside of it, that bacteria will be swept up along with the atmospheric air via the vacuum regulator into the air section of the fluid line and ultimately into the milk.

High levels of bacteria within milk present health risks to those who will consume the milk and the milk products derived from the milk such as cream and cheese. While downstream processes such as pasteurization at the milk processing plant are for reducing levels of unwanted bacteria, many milk marketing regulators will penalize a producer in the event that bacteria levels in a sample of tested milk exceeds an acceptable level. For example, the Milk and Milk Products Regulation (R.R.O. 1990, Regulation 761) enabled by the Milk Act in Ontario, Canada (R.S.O. 1990, CHAPTER M.12) specifies that milk being produced by a producer shall be tested for bacteria levels at least once per month. In order for tested milk to be considered grade 1, it must have less than 50,000 bacteria per milliliter of milk. In the event that tested milk has 50,000 or more bacteria per milliliter of milk, it is considered grade 2. If a series of milk tests results in the milk from a particular producer remaining at grade 2 over a threshold number of monthly tests, the producer will be held liable for a financial penalty the amount of which is based on the volume of milk. The producer's milk may ultimately be refused for marketing if the high bacteria levels persist over time. Meanwhile, the animals will continue to require milking in order to stay healthy, and the costs of disposing unmarketable milk will fall on the shoulders of the producer.

Due to the potentially significant financial penalties and disruptions accruing to a milk producer as a result of high bacteria levels in the milk, it is important for the producer to maintain bacteria levels to within an acceptable level.

SUMMARY OF THE INVENTION

The invention relates to drawing ozone gas into a fluid line of a dairy farm milking system in order to provide antibacterial treatment of fluid passing through the fluid line so as to kill air borne bacteria before it is drawn into milk being harvested and to kill bacteria that has been drawn into the milk being harvested. Advantageously, ozone gas is significantly more effective than chlorine even at low levels, and leaves no residue within the fluid line.

According to an aspect, there is provided a fluid line treatment kit for a dairy farm milking system having a vacuum subsystem for imparting vacuum within a fluid line, the fluid line treatment kit comprising at least one ozone gas source; a conduit associated with each ozone gas source configured to convey ozone gas to within the fluid line at a respective location; and a control system configured to trigger each ozone gas source to produce ozone gas while the vacuum subsystem is actuated, wherein vacuum imparted by the vacuum subsystem in the fluid line draws ozone gas via the at least one conduit into and through the fluid line.

According to another aspect, there is provided a dairy farm milking system comprising a fluid line having liquid and air sections; a vacuum subsystem for imparting vacuum within the fluid line; at least one milking unit in fluid communication with the fluid line for introducing milk into the liquid section of the fluid line; at least one ozone gas source configured to provide ozone gas to within the fluid line; and a control system configured to trigger each ozone gas source to produce ozone gas while the vacuum subsystem is actuated, wherein vacuum imparted by the vacuum subsystem in the fluid line draws ozone gas into and through the fluid line.

According to another aspect, there is provided a method for treating a fluid line of a dairy farm milking system having a vacuum subsystem for imparting vacuum within the fluid line, the method comprising configuring at least one ozone gas source to be in fluid communication with the fluid line; triggering at least one ozone gas source to produce ozone gas; and causing the ozone gas to be drawn within and through the fluid line using vacuum imparted within the fluid line.

BRIEF DESCRIPTION OF THE DRAWING

Embodiments of the invention will now be described with reference to the appended drawings in which.

DETAILED DESCRIPTION

Figure 1:
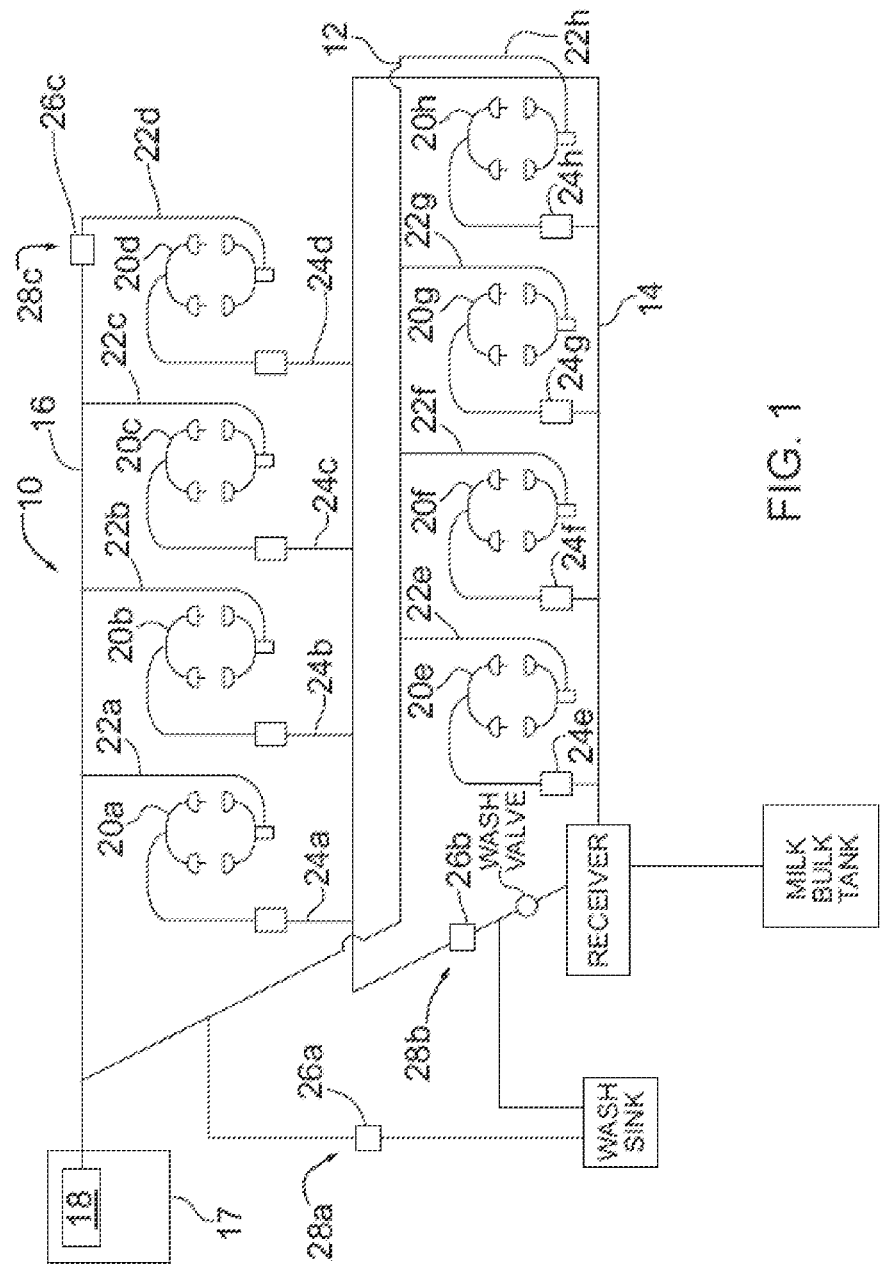
FIG. 1 is a schematic diagram of a dairy farm milking system with components for fluid line treatment, according to an embodiment.

Turning now to FIG. 1, there is shown a dairy farm milking system 10 with integrated fluid line treatment components, according to an embodiment. The dairy farm milking system 10 includes a fluid line 12 having a liquid section 14 and an air section 16, and a vacuum subsystem 17 including a vacuum pump 18 in fluid communication with the fluid line 12 for imparting a vacuum within the fluid line 12. In this embodiment, the vacuum pressure is about 11 to about 16 pounds per square inch (PSI). Eight milking units 20a, 20b, 20c, 20d, 20e, 20f, 20g, 20h are in fluid communication with the fluid line 12. The milking units 20a-h each include an air tube 22a-h coupled to the air section 16 of the fluid line 12, and a milk tube 24a-h coupled to the liquid section 14 of the fluid line 12 for introducing harvested milk to the fluid line 12.

In this embodiment, the fluid line treatment kit components include three ozone gas sources 26a, 26b and 26c configured to provide ozone gas to within the fluid line 12 via respective holes created at respective positions 28a, 28b, and 28c along the fluid line 12. In this embodiment, position 28a is along the liquid section 14 of the fluid line 12 within the milk house, position 28b is at a different position along the liquid section 14 of the fluid line 12 within the milk house, and position 28c is along the air section 16 of the fluid line 12 running above the stalls. The ozone gas sources 26a-c in this embodiment are each ozone gas generators positioned within a respective moisture-resistant storage box 27a-c (only storage box 27a is shown, in FIG. 4), along with a respective dryer (not shown).

Figure 4:
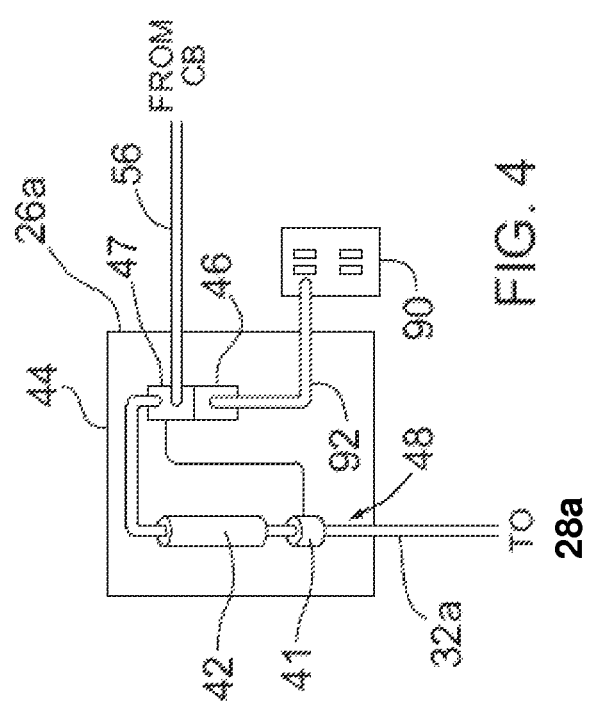
FIG. 4 is an elevational view of components of an ozone gas source within a storage box, according to an embodiment.

Ozone gas sources 26a, 26b and 26c are generally of the same construction, in this embodiment. As shown in FIG. 4, ozone gas source 26a incorporates an ozone gas generator 42 for generating ozone gas. Ozone gas generator 42 is positioned within a storage box 44 along with a control board 46 having a solid state relay switch 47 to which it is electrically connected. The solid state relay switch 47 is also electrically connected to relay terminal 55 of control box CB and thereby operable by control box CB as will be described. In this embodiment, ozone gas generator 42 is a corona discharge ozone gas generator operating at 12 VDC from an 115V input to produce between 0.200 and 0.220 Milligrams/hour of ozone gas for conveying out of outlet 48 of ozone gas source 26a. The rate of ozone output by the ozone gas source 26a is preferably adjustable by service personnel or a consumer based on various factors including the volume of the lines, amount of ozone desired, regulations, and perhaps other factors. Ozone gas source 26a receives input power from electrical reception outlet 90 via electrical cord 92 and a 12 VDC power adaptor A in a known manner. Ozone gas source 26a could be powered at other levels depending on the needs of the implementation.

A respective conduit 32a-c extends from each ozone gas source 26a-c to its respective position 28a-c. In this embodiment, each conduit 32a-c includes a check valve 33a-c for blocking fluid from the fluid line 12 such as milk or air flowing back into each ozone gas source 26a-c.

A control system is configured to trigger each ozone gas source 26a-d to produce ozone gas while the vacuum subsystem 17 is imparting vacuum to the fluid line 12. The vacuum draws ozone gas via each conduit 32-c into and through the fluid line 12 thereby to control levels of unwanted bacteria within the fluid line 12.

In this embodiment, the control system includes a milker control box CB that includes a manual switch for controlling electrical power being provided via a receptacle 90 simultaneously to both the vacuum subsystem 17 and each of ozone gas sources 26a-c. The manual switch (not shown) simultaneously controls electrical power ON/OFF for both the vacuum subsystem 17 and the ozone gas sources 26a-c. As such, the ozone gas sources 26a-c are powered to generate ozone gas while the vacuum subsystem 17 is powered to impart vacuum to the fluid line 12, thus drawing air and liquid through the fluid line while also drawing ozone gas into and through the fluid line as it is being generated. In this embodiment, the 115V AC power is converted to 12 VDC for provision to the ozone gas sources 26a-c.

With the system having been configured as described above to put the ozone gas sources in fluid communication with the fluid line, the fluid line may be treated by triggering the ozone gas sources to produce ozone gas and causing the ozone gas to be drawn within and through the fluid line using the vacuum imparted within the fluid line. In doing so, the ozone gas is caused to come into contact in the fluid line with air borne bacteria that may be drawn up into the fluid line as described above, and also is caused to come into contact with any bacteria that was initially air borne but that has subsequently been intermixed with the liquid in the fluid line, such as the milk Contacting the bacteria with the ozone gas tends to kill the bacteria.

Although embodiments have been described with reference to the drawings, those of skill in the art will appreciate that variations and modifications may be made without departing from the spirit and scope thereof as defined by the appended claims.

For example, an alternative implementation could include only one ozone gas source configured to provide ozone gas to within the fluid line at a position along the fluid line. The position could be along the liquid section of the fluid, along the air section of the fluid line, or at the vacuum subsystem.

Figure 2:
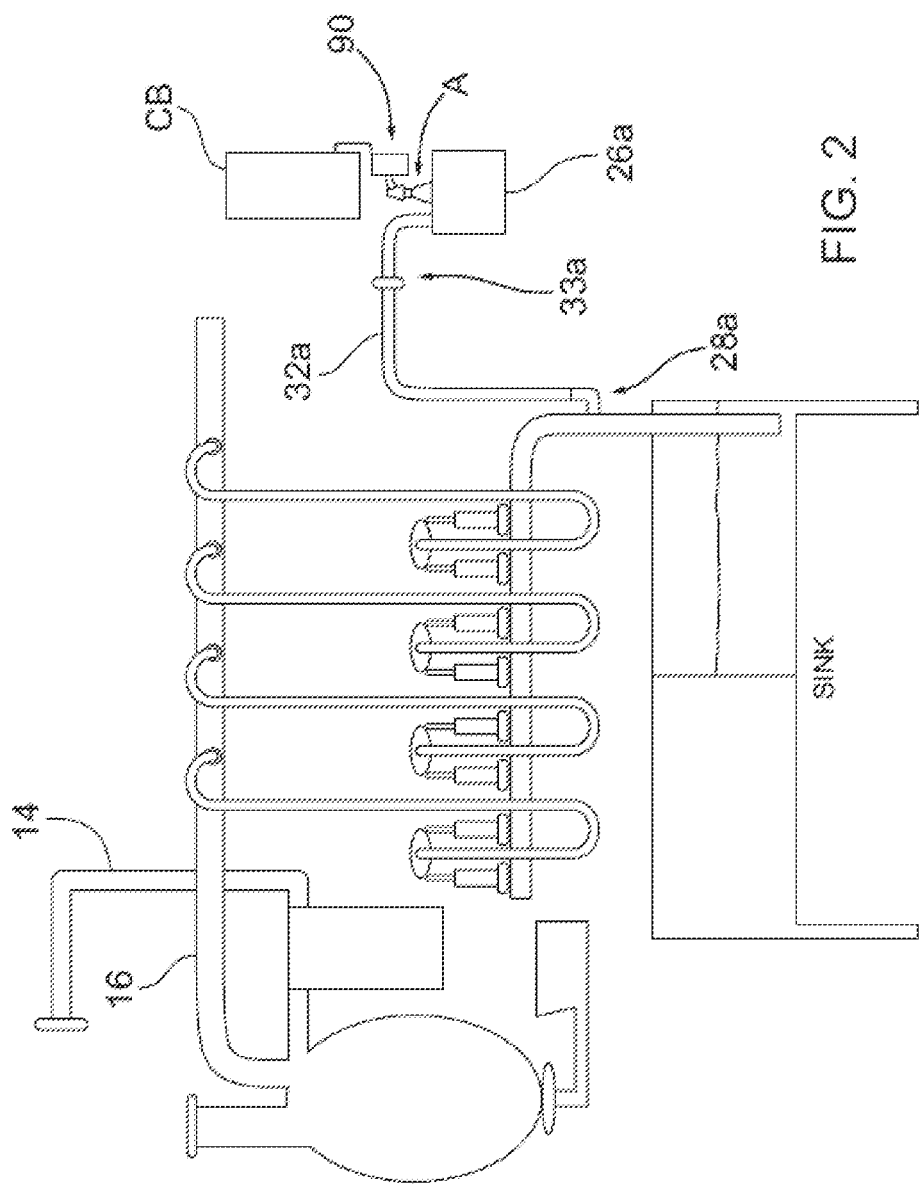
FIG. 2 is an elevation view of parts of a dairy farm milking system with components for fluid line treatment, within a milk house of the dairy farm.
Figure 3:
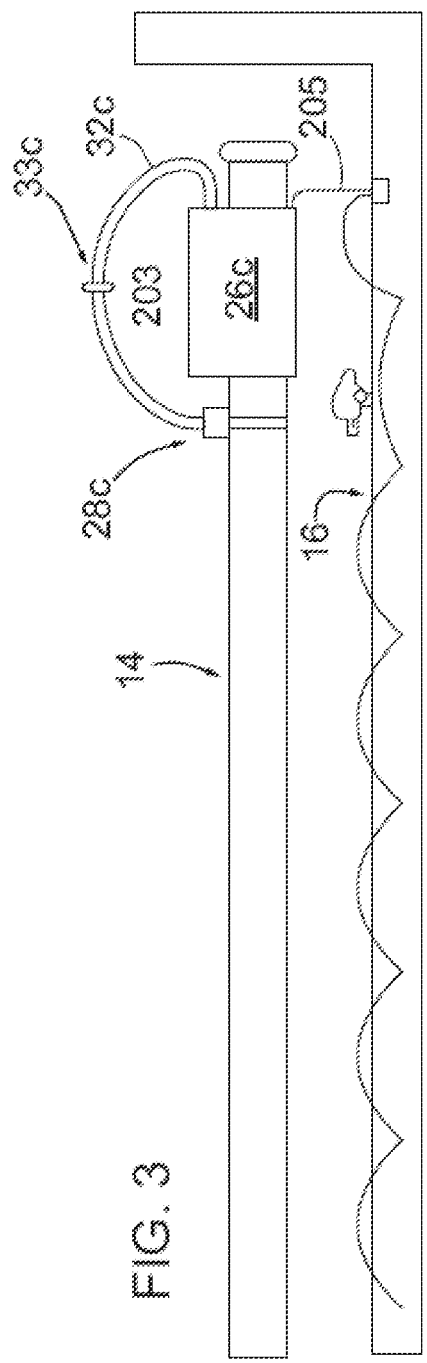
FIG. 3 is an elevation view of a portion of air and liquid sections of a fluid line of a dairy farm milking system running above stalls, and components for fluid line treatment.

FIG. 2 is an elevation view of parts of a dairy farm milking system with components for fluid line treatment, within a milk house of the dairy farm. FIG. 3 is an elevation view of a portion of air and liquid sections of a fluid line of a dairy farm milking system running above milking stalls. Various points along the fluid line of the milking system can be selected for providing ozone gas as described.

For example, in an embodiment, ozone may be drawn into the milk bulk tank by vacuum that is imparted to the fluid line providing water (ie. water line) during the process of rinsing the milk bulk tank. In particular, as is known, when it is desired to rinse a milk bulk tank, the milk bulk tank is filled with water from the bottom via a water line running first through valves in the control box CB, and then through a water pump inlet. Once the tank is filled, the water having been run through the milk bulk tank for rinsing is pumped back out of the milk bulk tank using a wash pump and circulated back into the milk bulk tank through the top of the tank or, in some cases, circulated back through another inlet into the bottom of the milk bulk tank. It has been observed that a vacuum is imparted to the water line (at this point clear of water due to closing of a valve by the control box CB) between the milk bulk tank and the control box CB, while the wash pump is pumping rinse water back out of the milk tank. While the vacuum is being imparted, or alternatively at any time the wash pump is being activated by the control box CB and the water line between the control box CB and the milk bulk tank, the control box CB can also signal an ozone gas source such as ozone gas source 26a to begin producing ozone. Ozone exiting the outlet 48 of such an ozone gas source 26a can be conveyed along conduit 32a and into the water line itself via a respective check valve. Alternatively, a separate pump could be used to pump ozone into the water line rather than have the ozone drawn solely by vacuum, or the pressure of ozone kept in a gas tank and not generated at the time of demand could be used to force ozone into the water line.

Furthermore, while embodiments have been described that introduce ozone gas directly into the air section or liquid section of the fluid line, the ozone gas could be introduced into the fluid line at the point at which the fluid lines interface with the vacuum subsystem/pump.

Alternatively, any number of ozone gas sources could be used in order to distribute an appropriate amount of ozone gas throughout the fluid line for effectively lowering bacteria counts, whether introduced at the air section, the liquid section, or at the vacuum subsystem/pump.

Furthermore, alternative embodiments may be provided that do not employ a check valve within the conduit that conveys ozone gas. In particular, some other mechanism or configuration that functions to discourage fluid from the fluid line retreating back into the ozone gas source could be used. For example, each ozone gas source could be positioned above its associated location along the fluid line so that it is gravity that reduces the opportunity for liquid to rise into the ozone gas source. A combination of check valve and such positioning may be employed.

Embodiments have been provided for retrofitting an existing dairy farm milking system using a fluid line treatment kit. However, alternative configurations of dairy farm milking systems that are more tightly integrated with the fluid line treatment components described herein may be provided. For example, a dairy farm milking system may include ozone gas sources directly coupled to the fluid line so as to provide ozone gas directly into the fluid line as described but without need for a conduit.

While embodiments have been described of a control system that employs a single manual switch to control electrical power simultaneously to the vacuum subsystem and the ozone gas sources, alternative implementations of control systems may involve triggering provision of electrical power to the ozone gas sources in an indirect manner, such as by detecting the application of electrical power to the vacuum subsystem and automatically applying power to the ozone gas sources. Still further, alternative implementations may involve detecting the application of a threshold vacuum pressure to the fluid line itself and, in response, automatically triggering application of electrical power to the ozone gas sources. This may be implemented with use of a vacuum switch.

Embodiments that involve providing electrical power to an ozone generator automatically in response to the detection of a threshold level of vacuum pressure within the fluid line, or automatically in response to the detection of electrical power having been applied to the vacuum subsystem of the dairy farm milking system are convenient for the producer. However, a system including a switch that must be manually activated by the producer for providing electrical power to a respective ozone gas source, or to all ozone gas sources, may alternatively be provided.

An alternative ozone gas source may be used that stores ozone gas in one or more containers such as a pressurized gas cylinder. With such an implementation, rather than actually generating the ozone gas on demand, ozone gas would be produced for drawing into the fluid line simply by releasing the ozone gas from the gas cylinder while a normally-closed release valve associated with the gas cylinder is either electrically or manually triggered to be opened. While such a system would generally function, an on-demand ozone gas generator such as described herein is generally preferred because it tends to be more compact and does not require frequent refilling or replacement. Furthermore, regulations in a given jurisdiction relating to the pressurized storage of gases may require that pressurized gas cylinders be stored centrally, with a distribution network of piping extending from the cylinder area to one or more locations along the fluid line. As would be understood, such a configuration is complex and costly, and due to the length of the distribution piping may delay provision of ozone gas to within the fluid line.

While embodiments have been described that function to draw ozone gas into the fluid line whenever the vacuum subsystem is actuated, alternative embodiments are contemplated. For example, due to the increased uptake of atmospheric air from towards the floor of the barn during the milking cycle as compared to a cleansing/rinsing cycle (where the milking unit is not in position on an animal), a producer may choose to not produce ozone gas for drawing into the fluid line during the cleansing/rinsing cycle, while producing ozone gas only during the milking cycle. Such flexibility may be provided by configurations that permit control over the application of power to the ozone gas sources independently from the vacuum subsystem itself. This independent control may be governed and exercised by a computer system in a large-scale dairy farm milking system, involving inputs for decision-making such as detected levels of air borne bacteria, temperatures, season, history of bacteria levels and so forth. However, such control could alternatively be governed by the experience and judgement of the producer, and exercised using a manual switch.

What is claimed is:

1. A method for treating a fluid line of a dairy farm milking system having a vacuum subsystem for imparting vacuum within the fluid line, the method comprising:
   configuring at least one ozone gas source to be in fluid communication with the fluid line;
   triggering at least one ozone gas source to produce ozone gas; and
   causing the ozone gas to be drawn within and through the fluid line using vacuum imparted within the fluid line, wherein the triggering is automatic in response to actuation of the vacuum subsystem.

2. The method of claim 1, wherein the triggering is automatic in response to detecting application of electrical power from a power source to the vacuum subsystem.

3. The method of claim 1, wherein the triggering is automatic in response to detecting presence of a threshold vacuum pressure in the fluid line.

4. The method of claim 1, wherein the ozone gas is caused to be drawn within the fluid line from a location associated with at least one of: an air section of the fluid line, a liquid section of the fluid line, and the vacuum subsystem.

* * * * *